US00PP29281P2

(12) United States Plant Patent
Hansen

(10) Patent No.: US PP29,281 P2
(45) Date of Patent: May 8, 2018

(54) ***PEROVSKIA* PLANT NAMED 'BLUE JEAN BABY'**

(50) Latin Name: *Perovskia atriplicifolia (Benth.)*
Varietal Denomination: Blue Jean Baby

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days. days.

(21) Appl. No.: 15/530,301

(22) Filed: Dec. 20, 2016

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt

(57) ABSTRACT

The new and distinct cultivar of ornamental, hardy, Russian Sage plant, *Perovskia* 'Blue Jean Baby' with short, dense habit of strong erect stems that remain upright through the growing season. The new plant is vigorous with many large, densely-arranged lavender-blue flowers on branched stems. Foliage is silvery-green, highly-dissected, pinnately-compound with crenate margins and is retained well and keeps its leaves throughout the growing season.

1 Drawing Sheet

Botanical classification: *Perovskia atriplicifolia* (Benth.).
Variety denomination: 'Blue Jean Baby'.

BACKGROUND OF THE INVENTION

The present invention relates to a new and distinct plant of Russian sage, botanically known as *Perovskia atriplicifolia* 'Blue Jean Baby' and will be referred to hereinafter also by its cultivar name 'Blue Jean Baby' and the new plant. The new plant cultivar of *Perovskia* is a hardy herbaceous perennial grown for landscape use.

*Perovskia* 'Blue Jean Baby' is from seed from a selfing of siblings in population of the proprietary unreleased hybrid grex known as K10-01 collected by the inventor in the fall of 2011 at a wholesale perennial nursery in Zeeland, Mich. All subsequent evaluations were performed in a full-sun trial garden at the same nursery with loamy sand soil and irrigation and fertilizer as required. The single seedling plant was selected for further evaluation during the summer of 2012 and given the breeder designation "11-01-04." The plant was propagated by stem cuttings at the same nursery in Zeeland, Mich. and the original plant and the cuttings evaluated over the next two years until final approval for introduction in the summer of 2014. The resultant asexually propagated cuttings have been stable and identical to the original plant in successive asexual propagations.

No plants of *Perovskia* 'Blue Jean Baby' have been sold in this country, under this or any name, or anywhere in the world, prior to the filing of this application, nor has any disclosure of the new plant been made prior to the filing of this application with the exception of that which was disclosed within one year of the filing of this application and was derived either directly or indirectly from the inventor.

SUMMARY OF THE INVENTION

*Perovskia atriplicifolia* 'Blue Jean Baby' differs from its parent as well as all other hardy Russian sage known to the inventor in a combination of traits. The following characteristics in combination distinguish 'Blue Jean Baby' from all other *Perovskia* plants known to the inventor:

1. Short dense habit with erect strong stems that remains upright through the growing season;
2. Long flowering season of large, densely-arranged, lavender-blue flowers on short branched stems;
3. Effective flowering time extended with smoky purple calyxes;
4. Silvery-green, highly-dissected, pinnately compound and serrated foliage retained throughout growing season.
5. Vigorous growth rate.

The nearest comparison plants known to the inventor are the parent plant *Perovskia* 'LISSLITT' U.S. Plant Pat. No. 20,845, 'Peek-a-Blue' (not patented), and 'Rocketman' U.S. Plant Pat. No. 27,526 and 'Denim 'n Lace' U.S. Plant Pat. No. 28,445. Compared to the cultivar 'LISSLITT', *Perovskia* 'Blue Jean Baby' is slightly taller with more upright stems less prone to lodging, and more upright and denser branching. Compared to 'Peek-a-Blue' the new plant has denser more upright branches and coarser leaf divisions and is less prone for foliage to turn yellow and drop lower leaves. Compared to 'Denim 'n Lace' the new plant has less dense terminal calyxes, broader habit, with more stems and more vigorous.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color. The plant used in the photograph is a five-year old plant grown in full sun field in loamy sand soil in trial gardens of a nursery in Zeeland, Mich.

DETAILED BOTANICAL DESCRIPTION

Figure 1:
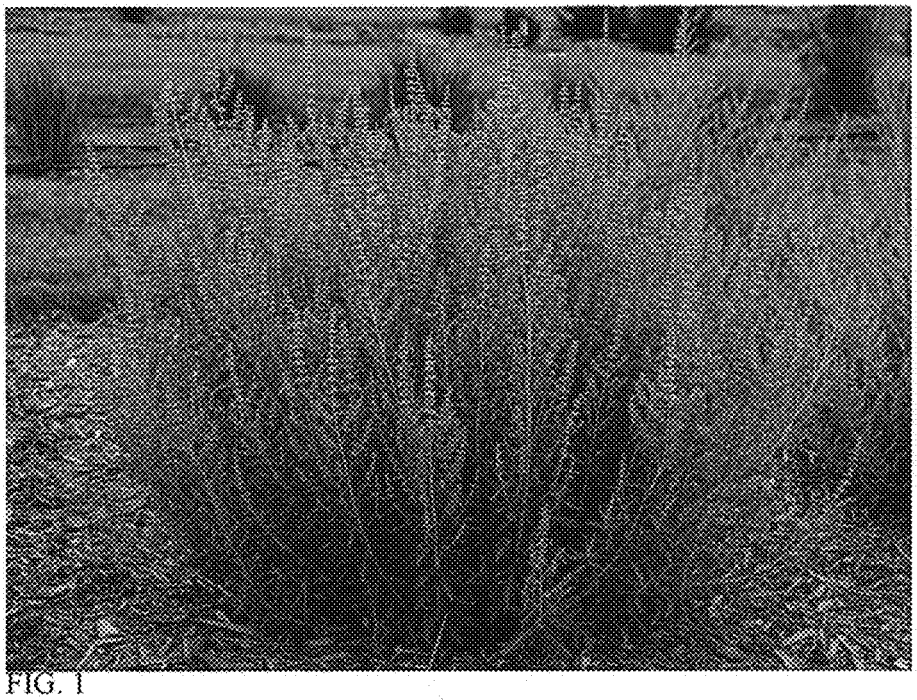
FIG. 1 shows 'Blue Jean Baby' in the landscape.
Figure 2:
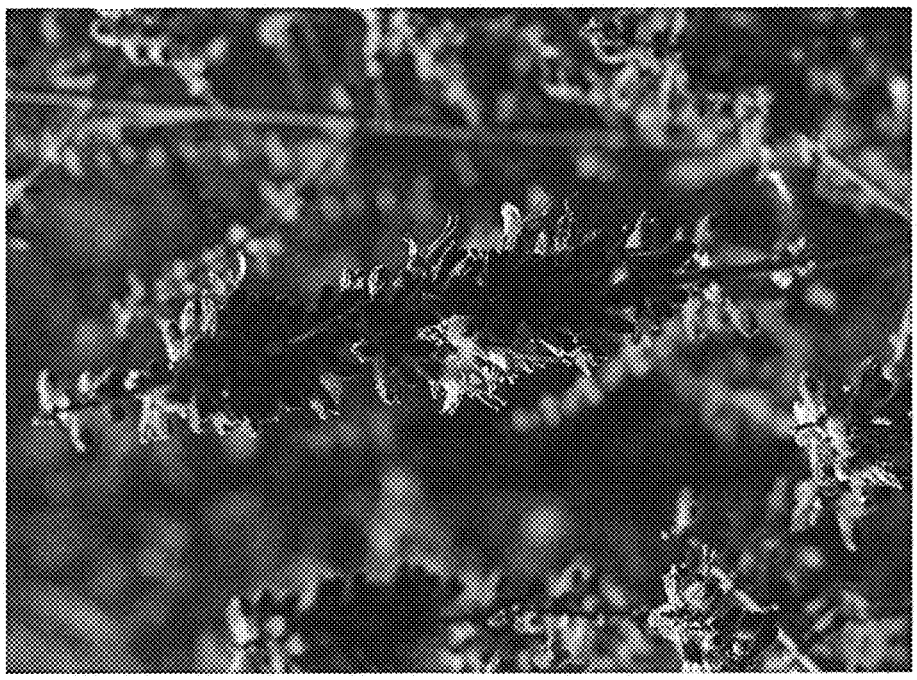
FIG. 2 shows a close-up of the flower stems of 'Blue Jean Baby'.

The following is a detailed description of *Perovskia atripicifolia* 'Blue Jean Baby' as observed and compared to other cultivars for five years in trial gardens and production fields at a nursery in Zeeland, Mich. The following description is of a five-year old plant of *Perovskia atripicifolia* 'Blue Jean Baby' in a full-sun trial garden in Zeeland, Mich. with limited irrigation as needed and without any pinching or plant growth regulators. The new plant has not been observed under all possible environments, and the phenotype may vary slightly with different environmental conditions, such as temperature, light, fertility, moisture and maturity levels, but without any change in the genotype. The color descriptions are in accordance with the 2001 edition of The Royal Horticultural Society Colour Chart of The Royal Horticultural Society, London, England, except where common dictionary color terms are used.

Plant habit: Upright and dense shape; oppositely branched; deciduous, semi-woody sub-shrub usually dying to the ground in most Michigan winters and re-sprouting with new stems from the base each spring; about 64 stems per plant;

Plant size: To about 100.0 cm in height, average stem height of about 92.0 cm, and about 115.0 cm in width about 25 cm above soil;

Root description: Fibrous; color nearest RHS 155D;

Propagation: Stem cuttings; root initiation occurs in about 14 days at a temperature of 20° C.;

Growth rate: Vigorous;

Crop time: About 10 to 14 weeks to produce flowering plant from rooted plug;

Stem description: Quadangular; oppositely branched; young portions lanulose; older stems becoming woody at base; average about 92.0 cm long and about 7.0 mm across near base; about 30 branches per stem; with herbal fragrance;

Stem color: Between RHS 191B and RHS 191C;

Internode length: Average 3.0 cm;

Internode color: Same as surrounding stem;

Branches: Quadangular; opposite; lanulose; average about 55° angle above horizontal; lower branches about 19.0 cm long and about 3.0 mm diameter, decreasing distally to upper branches about 6.0 cm long and about 1.0 mm diameter;

Branch color: Nearest RHS 191D;

Foliage description: Opposite, broadly ovate; compounded lobed, palmately cleft nearly to midrib; acute apex and lobes, narrowly attenuate base; margin lobed to crenate, farinose on abaxial and puberulent on adaxial surface; to about 7.0 cm long and about 3.8 mm wide, shorter in distal region, average about 5.0 cm long and about 2.0 cm wide; with herbal fragrance;

Leaf color: Adaxial blend between RHS N138B and RHS 191B; abaxial blend between RHS N138C and RHS 191B;

Leaf venation: Pinnate; glandular adaxial and abaxial;

Vein color: Main adaxial vein nearest RHS 147B; abaxial midrib between RHS 145C and RHS 145D;

Petiole: Flattened abaxial to adaxial; sessile to about 9.0 mm long and about 1.5 mm across, average about 3.5 mm long and about 1.2 mm across at stem;

Petiole color: Adaxial nearest RHS 147B; abaxial between RHS 145C and RHS 145D;

Peduncle: Main stems vertical, branched verticillate panicle; about 10.0 cm tall above last branch and about 2.5 cm across; total inflorescence portion average about 50.0 cm tall and about 12.0 cm wide;

Peduncle color: Proximally nearest RHS 191D, distally between RHS 191B and RHS 191A;

Pedicel: Terete; glabrous; about 1.2 mm long and 0.5 mm diameter;

Pedicel color: Nearest RHS 138B with tinting of nearest RHS N79B;

Flower buds about one day prior to opening: About 9.0 mm long and about 2.0 mm wide; long ovoid; rounded apex; rounded base; abaxial calyx with dense pubescence about 1.0 mm long;

Bud color: Abaxial calyx hairs nearest RHS 83D; abaxial calyx base nearest RHS 138C with veins and tinting to solid nearest RHS N79B with increasing light exposure; extended unopened petal portion between RHS 96C and RHS 96B;

Flowers: Perfect, zygomorphic, bilabiate with upper and lower lip fused in about basal 6.5 mm; about 14.0 mm long and about 7.0 mm across; face opening to nearly flat; up to 18 flowers per verticil and over 800 per main stem;

Flower attitude: Outward and slightly drooping;

Fragrance: Slight herbal;

Corolla: Glabrous abaxial, adaxial throat puberulent; bilabitate; upper lip four-lobed, each with rounded apex and about 1.0 mm across at fusion and about 9.0 mm long, together about 6.0 m across, fused in basal 7.5 mm; lower lip entire, nearly flat with rounded apex; about 9.0 mm long and about 2.0 mm wide at fusion point; basal 5.0 mm fused into tube; tube about 2.5 mm in width;

Corolla color: Adaxial upper and lower lips nearest RHS 94B, adaxial tube lighter than RHS 92D and proximal one half of fused lips nearest RHS 92D; distal upper and lower lips abaxial nearest RHS 94B, distal one half of tube lighter than RHS 94D and proximal one half of tube nearest RHS 92D;

Gynoecium: One pistil;

*Style*.—About 6.0 mm long and about 0.2 mm diameter; color white, lighter than RHS 155D.

*Stigma*.—Bifurcate in the terminal 0.5 mm, about 0.3 mm across; color white, lighter than RHS 155D.

*Ovary*.—Oblong globose; about 1.0 mm long and 0.7 mm across; color nearest RHS 145C.

Androecium: Four, in two sets, two longer and fertile and two shorter and sterile; stamens adnate to corolla about 3.0 mm from base;

*Filaments* (*fertile pair*).—Exserted about 2.0 mm beyond lower lip; about 7.0 mm in length and less than about 0.5 mm in width; color nearest RHS 155D at base and gradually developing to nearest RHS 77D toward apex.

*Filaments* (*sterile pair*).—Fused to upper lip, about 3.0 mm long and less than 0.5 mm diameter; color nearest RHS 155D at base and nearest RHS 77D in about apical 0.5 mm.

*Anther*.—Fertile pair elliptic; about 0.5 mm long and 0.2 mm across, versatile; color nearest RHS 79A; sterile pair flattened ovoid, about 0.5 mm long and about 0.3 mm diameter; color nearest RHS 79A.

*Pollen*.—Abundant on fertile anthers; color nearest RHS 11D.

Calyx: Tubular campanulate; about 6.0 mm long and about 2.0 mm across; made up of five sepals fused at base in the proximal about 5.0 mm with apical about 1.0 mm separate; entire, apex acute; outside densely pubescent and glandular with hairs about 1.0 mm long, inside glabrous; persistent for weeks after flower abscission and drop;

Calyx color: Abaxial color at flowering and after base nearest RHS 138C with veins and tinting in higher light exposure nearest RHS N79B to solid RHS N79B in highest light exposures, and dense hairs nearest RHS 83D; adaxial color nearest RHS 147D with veins nearest RHS 187A;

Seed: Spatulate in outline, rounded apex and attenuate base; up to four per flower, typically one per flower; about 2.0 mm long and about 1.0 mm diameter at widest portion and about 0.5 mm thick; color nearest RHS 200A; Hardiness of the new plant is at least U.S.D.A. zones 4 to 9. The new plant is highly resistant to drought once established.

*Pest and disease resistance.*—Russian sage is typically resistant to deer and rodent browsing. The new plant is less prone to yellowing foliage and lower leaf drop than other known Russian sage cultivars. No other susceptibility or resistance to diseases or pests has been observed except that which is common to *Perovskia.*

It is claimed:

1. A new and distinct cultivar of hardy Russian sage plant, *Perovskia* 'Blue Jean Baby' as herein described and illustrated.

* * * * *